United States Patent [19]

Crump et al.

[11] Patent Number: 5,447,575
[45] Date of Patent: Sep. 5, 1995

[54] DEGRADABLE CHELANTS HAVING SULFONATE GROUPS, USES AND COMPOSITIONS THEREOF

[75] Inventors: Druce K. Crump, Lake Jackson; David A. Wilson, Richwood, both of Tex.

[73] Assignee: The Dow Chemical Company, Midland, Mich.

[21] Appl. No.: 289,874

[22] Filed: Aug. 12, 1994

Related U.S. Application Data

[60] Continuation-in-part of Ser. No. 134,783, Oct. 12, 1993, Pat. No. 5,389,594, which is a division of Ser. No. 7,947, Jan. 22, 1993, Pat. No. 5,258,141, which is a division of Ser. No. 708,534, May 31, 1991, Pat. No. 5,208,369.

[51] Int. Cl.$^6$ ............................ B08B 3/04; C11D 1/04
[52] U.S. Cl. .................... 134/42; 134/22.14; 134/22.19; 252/546
[58] Field of Search ................ 134/22.14, 22.19, 42; 252/546

[56] References Cited

U.S. PATENT DOCUMENTS

| | | | |
|---|---|---|---|
| 2,130,505 | 9/1938 | Münz | 562/566 |
| 2,407,645 | 9/1946 | Bersworth | 562/565 |
| 2,413,856 | 1/1947 | Bersworth | 524/239 |
| 2,428,353 | 10/1947 | Bersworth | 514/21 |
| 2,532,391 | 12/1950 | Bersworth | 562/565 |
| 2,806,060 | 9/1957 | Bersworth et al. | 562/564 |
| 3,091,522 | 5/1963 | Hemwall | 71/1 |
| 3,591,510 | 7/1971 | Zenk . | |
| 3,592,830 | 7/1971 | Nasser | 556/448 |
| 3,635,829 | 1/1972 | Yang | 252/562 |
| 3,652,432 | 3/1972 | Pollack et al. | 204/141.5 |
| 3,683,014 | 8/1972 | Yang | 439/737 |
| 3,689,544 | 9/1972 | Scanlon et al. | 562/564 |
| 3,703,545 | 11/1972 | McCrary | 562/102 |
| 3,726,912 | 4/1973 | McCrary et al. | 562/102 |
| 3,780,099 | 12/1973 | Scanlon et al. | 562/564 |
| 3,780,100 | 12/1973 | Scanlon et al. | 562/564 |
| 3,988,367 | 10/1976 | Gaudette et al. | 562/565 |
| 4,352,751 | 10/1982 | Wieder et al. | 260/112 R |
| 4,432,907 | 2/1984 | Wieder et al. | 260/429.2 |
| 4,454,046 | 6/1984 | Wallace et al. | 210/698 |
| 4,614,644 | 9/1986 | Lampton, Jr. et al. | 423/226 |
| 4,668,532 | 5/1987 | Moisan et al. | 427/97 |
| 4,764,306 | 8/1988 | Login | 260/404.5 |
| 4,812,263 | 3/1989 | Login | 260/404.5 |
| 4,830,838 | 5/1989 | Kent et al. | 423/226 |
| 4,965,211 | 10/1990 | Wieder et al. | 436/543 |

FOREIGN PATENT DOCUMENTS 0040882 12/1981 European Pat. Off. .
3337026 4/1985 Germany .
5139350 10/1980 Japan .

OTHER PUBLICATIONS

Chemical Abstract 100:174278v, 1984.
Chemical Abstract 101:125986m, 1984.

(List continued on next page.)

*Primary Examiner*—P. Achutamurthy

[57] ABSTRACT

New compounds are represented by Formula I:

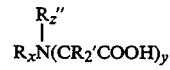

and salts and complexes thereof; wherein R is an alkyl group having at least one —SO$_3$H and at least one —OH; each R' is independently selected from hydrogen, an unsubstituted or inertly substituted alkyl group, an alkyl group substituted with a carbonyl group, with a carboxylic acid, salt or complexed carboxyl group, or an alkoxy group; R" is hydroxyalkyl and x+y+z=3 and are good chelants. The compounds are also biodegradable and are particularly useful in hard surface cleaners.

8 Claims, No Drawings

OTHER PUBLICATIONS

Chemical Abstract 106:69737v, 1987.
Derwent Abstract 14845A/08, 1976.
Derwent Abstract 47950S, 1969.
Derwent Abstract 88-156420/23, 1986.
Derwent Abstract 90-268524/36, 1988.
Derwent Abstract 21748D/13, 1979.
Derwent Abstract 85-105821/18, 1985.
Dr. P. A. Gilbert, "Environmental Pressures in Europe", *Soap/Cosmetics/Chemical Specialties for March*, pp. 27–31 (1990).
James M. Tiedje, "Microbial Degradation of Ethylenediaminetetraacetate in Soils and Sediments", *Applied Microbiology*, vol. 30, No. 2, pp. 327–329 (Aug. 1975).
"NTA:'health hazard'", *European Chemical News*, p. 20, (Jan. 21, 1985).
Laurent Sif and Hakan Bjorndal, "Effect of Complex Formers on the Aquatic Environment, NTA, EDTA and DTA", *IVL Report*, (Dec. 1988).

DEGRADABLE CHELANTS HAVING SULFONATE GROUPS, USES AND COMPOSITIONS THEREOF

This application is a continuation-in-part of the application Ser. No. 08/134,783, filed Oct. 12, 1993, U.S. Pat. No. 5,389,594, which is a divisional of application Ser. No. 08/007,947 filed Jan. 22, 1993, U.S. Pat. No. 5,258,141, which is a divisional of application Ser. No. 07/708,534 filed May 31, 1991, U.S. Pat. No. 5,208,369, all of which are incorporated herein in their entireties.

Chelants or chelating agents are compounds which form coordinate-covalent bonds with a metal ion to form chelates. Chelates are coordination compounds in which a central metal atom is bonded to two or more other atoms in at least one other molecule or ion (called ligand) such that at least one heterocyclic ring is formed with the metal atom as part of each ring.

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry. Some of these activities result in chelants entering the environment. For instance, agricultural uses or detergent uses may result in measurable quantities of the chelants being in water. It is, therefore, desirable that chelants degrade after use.

Biodegradability, that is susceptibility to degradation by microbes, is particularly useful because the microbes are generally naturally present in environments into which the chelants may be introduced. Commonly used chelants like EDTA (ethylenediamine tetraacetic acid) are biodegradable, but at rates somewhat slower than some environmentalists would prefer. (See, Tiedje, "Microbial Degradation of Ethylenediaminetetraacetate in Soils and Sediments," Applied Microbiology, Aug. 1975, pp. 327-329.) It would be desirable to have a chelating agent, which degrades faster than EDTA or other commonly used chelants.

While degradation of the chelant compounds themselves is an important factor in ascertaining their fate in the environment, it is also important to consider the form(s) in which the compound is likely to be found in a natural environment like a lake, river or soil. In contact with such environments, chelants can frequently be expected to be in the form of their chelates with metals present in the environment or metals acquired in use of the chelant. The specific metal chelated depends on the metals present, their relative concentrations and availability, and the relative affinity (e.g. as expressed by stability constants) of the chelant for each metal present. It is often important that the chelant degrade well in the form of its iron, copper, manganese or calcium complexes. It would be desirable for a chelant compound to degrade in the form(s) it is most likely to be found in the environment. This form is commonly the iron complex. (See, Laurent et al., IVL Report, "Effect of Complex Formers on the Aquatic Environment, NTA, EDTA and DTPA", Inst. Water and Air Conservation Research (IVL), Stockholm, Pub. B921, Dec. 1988.

Some chelants are at least somewhat biodegradable, but have other disadvantages that reduce their suitability for applications that may result in their presence in water. For instance, NTA (nitrilotriacetic acid) has given indications of carcinogenicity. (See, National Cancer Institute Report NCI-CG-TR-6, NIH-77-806 January, 1977.)

SUMMARY OF THE INVENTION

In one aspect the invention is a compound represented by Formula I:

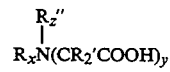

and salts and complexes thereof; wherein R is an alkyl group having at least one —SO$_3$H and at least one —OH; each R' is independently selected from hydrogen, an unsubstituted or inertly substituted alkyl group, an alkyl group substituted with a carbonyl group, with a carboxylic acid, salt or complexed carboxyl group, or an alkoxy group; R" is hydroxyalkyl; and x, y and z are integers; x and y each being at least 1, such that x+y+z=3.

In another aspect, the invention is the method of using compounds of Formula I to chelate metal ions.

In yet another aspect, the invention is a washing composition comprising an organic detergent surfactant selected from the group consisting of anionic detergents, cationic detergents, nonionic detergents, ampholytic detergents, zwitterionic detergents, and mixtures of such detergents suitable for use in water and at least one water-soluble salt of the acids of Formula I selected from the group consisting of alkali metal salts, ammonium salts, and alkyl ammonium salts. The ratio by weight of the detergent surfactant to the salts of the acids of Formula I preferably is in the range of about 100:1 to about 3:2.

In the field of gas conditioning, the invention includes a fluid comprising contacting the fluid with an aqueous solution of at least one lower valence state polyvalent metal chelate of Formula I. Additionally the invention includes a fluid comprising contacting said fluid with an aqueous solution at a pH suitable for removing H$_2$S wherein said solution contains at least one higher valence polyvalent metal chelate of Formula I Compounds of the invention are effective chelants, and are advantageously especially useful in maintaining the bleaching effect of bleaching compositions.

DETAILED DESCRIPTION OF THE INVENTION

The invention includes compounds of Formula I:

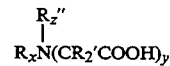

and salts and complexes thereof; wherein R is an alkyl group having at least one —SO$_3$H and at least one —OH group and each R' is independently selected from hydrogen, an unsubstituted or inertly substituted alkyl group, an alkyl group substituted with a carbonyl group, with a carboxylic acid, salt or complexed carboxyl group, an alkoxy group, a hydroxyalkyl group; R" is hydroxyalkyl and x, y and z are integers, x and y each being at least 1 such that x+y+z=3. For instance, R' can be —CH$_3$, —C$_2$H$_5$, —CH$_2$COCH$_3$ (substituted with a carbonyl group), —CH$_2$COOH (substituted with a carboxylic acid group), —CH$_2$OCH$_3$, —CH$_2$CHOHCH$_3$ and the like. R' preferably, for reasons of solubility, has from 1 to about 20 carbon atoms, more preferably from 1 to about 6, most preferably from 1 to about 4 carbon atoms, even more preferably 1 carbon atom. While R is optionally inertly substituted, it is preferably unsubstituted. R' is preferably H or alkyl or alkyl group substituted with a carboxylic acid, salt or complexed carboxyl group; more preferably H, methyl or carboxymethyl group; most preferably H, each for reasons of availability of starting materials. R" is a hydroxyalkyl group preferably having from 1 to about 6, more preferably from about 2 to about 4, most preferably from about 2 to about 3 carbon atoms. Each of x, y and z are integers; x, an integer of from 1 to 2; y of from 1 to 2; and z of from 0 to 1. Preferably, z is 0. For reasons of increased complex stability, x is preferably 1 and y is preferably 2.

Preferably, for reasons of degradability and bleach stabilization, R has one —$SO_3H$ group and one —OH group; R is preferably about $C_2$-$C_7$, more preferably, for reasons of ready availability of raw materials, about $C_3$-$C_4$, most preferably $C_3$; the —OH and —$SO_3H$ can be in any position on R, but preferably each is on a different carbon atom and more preferably they are on adjacent carbon atoms. Most preferably, the —OH is on the carbon atom beta to the carbon atom having the nitrogen, and the —$SO_3H$ is on a carbon atom gamma to the carbon atom having the nitrogen (2-hydroxypropyl sulfonic acid group).

By inert substitution is meant substitution which does not undesirably affect the chelating ability of the compounds, and prefereably does not undesirably affect the degradability of the compounds. Most preferably, effects of the substituents on chelating ability and degradability are balanced to achieve a compound with desirable chelating and degradation qualities, and somewhat more chelating ability or degradability than is found in the corresponding compound having hydrogen atoms rather than inert substituents. Those skilled in the art can achieve such balance without undue experimentation. Suitable inert substituents include alkyl, alkoxy, carboxyalkyl or combinations thereof (all preferably from 1 to about 6 carbon atoms, most preferably from about 1 to about 3 carbon atoms, and all suitably branched or linear.)

Preferred compounds of Formula I where z is 0 include nitrilo-N,N-bis(carboxymethyl)-N-2-hydroxypropyl sulfonic acid; nitrilo-N,N-bis(carboxymethyl)-N-3-hydroxypropyl -2-sulfonic acid; nitrilo-N,N-bis (carboxymethyl)-N-4-hydroxyheptyl-5-sulfonic acid; glycine, N,N-bis(2-hydroxypropyl sulfonic acid), aspattic acid, N-carboxymethyl-N-2-hydroxypropyl-3-sulfonic acid; alanine, N-carboxymethyl-N-2-hydroxypropyl -3-sulfonic acid; valine, N-carboxymethyl-N-2-hydroxypropyl -3-sulfonic acid; serine, N-carboxymethyl -N-2-hydroxypropyl-3-sulfonic acid with nitrilo-N,N-bis(carboxymethyl)-N-2-hydroxypropyl-3-sulfonic acid being more preferred because the raw materials for producing it are generally less expensive and more readily available. Preferred compounds of Formula I where z is 1 include glycine, N-2-hydroxyethyl, N-2-hydroxypropylsulfonic acid; glycine, N-2-hydroxypropyl-N-2-hydroxypropyl-sulfonic acid; glycine, N-3-hydroxypropyl-N-2-hydroxypropylsulfonic acid; and the like.

Compounds of Formula I are suitably prepared by reacting ammonia, glycine, amino acids, or ester amines with compounds such as halohydroxyalkyl sulfonic acids such as chloro-hydroxy-propane sulfonic acid. Any remaining amino hydrogens are optionally then reacted to provide carboxymethyl functionality such as done using chloroacetic acid or a functional equivalent thereof such as sodium or hydrogen cyanide and formaldehyde under alkaline conditions, such as by the procedures taught by Munz in U.S. Pat. No. 2,130,505 or as described by Bersworth in U.S. Pat. No. 2,673,213 and methods disclosed therein.

The compounds can also be prepared, for instance, by addition of epichlorohydrin (0.1 mole, 9.3 g) over a three hour period to a stirred aqueous solution of sodium bisulfite (0.1 mole, 10.4 g) while maintaining the temperature at about 80° C. After addition is complete, stirring at that temperature is continued for about one hour after which the mixture is allowed to cool to room temperature. The resulting solution or slurry is then added to a stirred excess of concentrated aqueous ammonia (1 mole or greater) and allowed to stir for about one hour at room temperature. The temperature is then raised to about 80° C. for an hour with reflux. Following the reaction at the elevated temperature, excess ammonia may be removed by stripping with nitrogen at reflux temperature with or without vacuum. When the ammonia level is reduced to a minimum, the resulting yield is essentially 1-amino-2-hydroxypropyl sulfonic acid. The acid is then carboxymethylated using techniques familiar to those skilled in the art. For example, sodium hydroxide (0.2 moles, 8 g) is added to the stirred mixture, the temperature is brought to 100° C. or reflux, and then glycolonitrile (0.2 moles, 28.5 g 40 percent aqueous solution) is added slowly over about two hours while sparging with air or nitrogen. This yields iminodiacetic acid, N-2-hydroxypropylsulfonic acid. Other known methods of carboxymethylation may also be employed.

Alternatively, an alkanol amine may be reacted with the hydroxyalkylsulfonic acid compound in, preferably, an equimolar ratio, followed by carboxymethylation of the remaining amino hydrogens. For example, 3-chloro-2-hydroxypropylsulfonic acid is reacted with monoethanol amine in equimolar quantities, to yield primarily ethanolamine, N-2-hydroxypropyl sulfonic acid sodium salt. The remaining amino hydrogens are then carboxymethylated using procedures such as outlined above. Other alkanolamines may be used instead of ethanolamine, such as monoisopropanolamine, n-proanolamine, n-butanolamine, sec-butanolamine, t-butanol amine, or other lower hydroxyalkylamine. Also, other reactants may be used to provide the hydroxyalkyl sulfonic acid functionality instead of 3-chloro-2-hydroxypropylsulfonic acid, such as alkylepoxide sulfonic acids preferably having from about 3 to about 7 carbon atoms alkylolefin sulfonic acids. Variations on these synthetic methods are within the skill in the art.

The compounds of the invention are effective as chelants. Effectiveness as a chelant is conveniently measured by complexing the chelant with a metal such as copper such as by mixing an aqueous solution of known concentration of the chelant with an aqueous solution containing copper (II) ions of known concentration and measuring chelation capacity by titrating the chelant with copper in the presence of an indicator dye, using as an endpoint detector a photosensitive electrode.

The stability constant may be calculated by comparing potentiometric pH measurement of the chelant in the absence of and in the presence of known concentrations of metal ion as described in DETERMINATION AND USE OF STABILITY CONSTANTS by Martell and Motekaitis, VCH Publishers, 1988, pp. 14 and 21–27. Various methods may be employed to determine stability constant. Preferably, the compounds are at least as effective as EDTA.

Chelating capacity is not, however, a direct indicator of effectiveness in activities such as stabilizing bleach. For instance, hydroxyethyliminodiacetic acid (HEIDA) is effective in chelating, e.g. copper (294 mg copper per gram of chelate), but is relatively ineffective in stabilizing bleaches. Tests of relative effectiveness are conducted in solutions simulating cleaning formulations having bleaches and metal ions such as those tests described in the examples of the invention. In addition to chelating ability, a chelant must be resistant to degradation by or reaction with the bleaching agent to effectively stabilize a bleach or bleaching composition.

Compounds of the invention are preferably biodegradable. Biodegradability is indicated by degradation on exposure to bacteria. Standardized tests such as ASTM D-2667-82 are preferably used to determine biodegradability. In that test, a standardized sludge containing municipal waste treatment plant organisms is used to biodegrade the chelate in the presence of metal ions representative of those found in the environment including iron. Such a test simulates the environment encountered in a municipal waste treatment plant for screening the inherent biodegradability of non-volatile, water-soluble compounds.

The compounds of this invention are generally employed in the form of a water-soluble salts, notably alkali metal salts, ammonium salts, or alkyl ammonium salts. The alkali metal salts can involve one or a mixture of alkali metal salts although the potassium or sodium salts, especially the partial or complete sodium salts of the acids of Formula I are preferred because of their relatively low cost and enhanced effectiveness. Because the detergent formulations are generally used in alkaline aqueous systems, it is entirely feasible to use in their manufacture either the acids of Formula I itself or the partially neutralized free acids. The free acid group(s) will be converted to the appropriate salt at least as soon as the formulations are put to use in an alkaline environment.

Chelants of the invention are useful, for instance, in food products vulnerable to metal-catalyzed spoilage or discoloration; in cleaning and laundering products for removing metal ions, e.g. from hard water, that may reduce the effectiveness, appearance, stability, rinsibility, bleaching effectiveness, germicidal effectiveness or other property of the cleaning agents; in personal care products like creams, lotions, deodorants and ointments to avoid metal-catalyzed oxidation and rancidity, turbidity, reduced shelf-life and the like in pulp and paper processing to enhance or maintain bleaching effectiveness; in pipes, vessels, heat exchangers, evaporators, filters and the like to avoid or remove scaling, in pharmaceuticals; in metal working; in textile preparation, desizing, scouring, bleaching, dyeing and the like; in agriculture as in chelated micronutrients or herbicides; in polymerization or stabilization of polymers; in photography, e.g. in developers or bleaches; in the oil field such as for drilling, production, recovery, hydrogen sulfide abatement and the like.

In detergent compositions, bleach compositions, cleaning compositions and sequestrant (chelating agent) compositions, the chelants of the invention can be used to control the level of free heavy metal ions in the compositions themselves and in liquors e.g. wash liquors, prepared therefrom. The amount used, if used as a chelant, is advantageously from about 0.01 to about 40 weight percent, based on the total weight of the detergent constituents. The compositions generally comprise from about 1 to about 99.99, preferably from about 5 to about 30 weight percent detergent; optionally, from about 5 to about 40 weight percent builder; and, optionally, from about 3 to about 30 weight percent bleach.

Their advantageous action also includes bleaching agent stabilization, for example for sodium perborate, in detergents and in the bleaching of textiles, pulp or paper stock. Traces of heavy metals, such as iron, copper and manganese, are present in the washing powder itself, in the water and in the textile or pulp material, and they catalyze the decomposition of the sodium perborate or other bleaches. The chelants according to the invention bind these metal ions and prevent the undesirable decomposition of the bleaching system during storage and in the wash liquor. This enhances the efficiency of the bleaching system and reduces fiber damage.

In addition, enzymes, optical brighteners and scents are advantageously protected from heavy metal catalyzed oxidative decomposition.

In liquid cleaning formulations the novel chelants can be used as preservatives advantageously in an amount from about 0.05 to about 15 percent by weight, based on the total weight of the formulation.

In soaps the novel chelants prevent, for example, metal catalyzed oxidative decompositions.

Furthermore, they give excellent performance in detergents as builders for preventing precipitates and incrustations on the fabric.

The chelants can be used in industrial processes whenever precipitates of Ca, Mg and heavy metal salts are a nuisance and are to be prevented. They are used, for example, for preventing scale deposits and incrustations in kettles, pipelines, spray nozzles or generally on smooth surfaces.

They are suitably used for stabilizing phosphates in alkaline degreasing baths and to prevent the precipitation of lime soaps and as a result prevent the tarnishing of nonferrous surfaces and prolong the service lives of alkaline cleaning baths.

They can be used as chelants in alkaline derusting and descaling baths and also in electroplating baths and also in electroplating baths in place of cyanides as sequestrants of impurities.

The treatment of cooling water with the novel chelants prevents and redissolves scale deposits. Of advantage is the use in an alkaline medium, thereby removing corrosion problems.

In the polymerization of rubber the chelants of the invention are suitably used for preparing e.g. the redox catalysts used therein. They additionally prevent the precipitation of such compounds as iron hydroxide in an alkaline polymerization medium.

In the photographic industry, the novel chelants are suitably used in developer/fixing baths made up with hard water to alleviate precipitations that lead to fogging on films and photographs and alleviate deposits in the tanks. Iron(III)-complexing solutions are advantageously used in bleach fixing baths to replace less safe solutions.

In the textile industry, the chelants are suitably used for removing heavy metal traces during the manufacture and dyeing of natural and synthetic fibers, thereby preventing many problems, such as dirt spots and stripes on the textile material, loss of luster, poor wettability, unlevelness and off-shade dyeings.

In the paper industry, the chelants are suitably used for eliminating heavy metal/iron ions. Iron deposits on paper lead to hot spots where oxidative, catalytic decomposition of the cellulose starts.

Exemplary of various other uses are applications in pharmaceuticals, cosmetics and foodstuffs where metal catalyzed oxidation of olefinic double bonds and hence rancidification of goods is prevented. The chelates are also useful as catalysts for organic syntheses (for example air oxidation of paraffins, hydroformylation of olefins to alcohols).

In plant nutrition, heavy metal deficiencies are remedied by using Cu, Fe, Mn, Zn complexes. Heavy metals are added as chelates to prevent their precipitation in the form of biologically inactive, insoluble salts.

Further fields of application for the novel chelants are gas washing, conditioning or scrubbing (of e.g. flue, geothermal, sour, synthesis, process, fuel, or hydrocarbon gas) to remove at least one acidic gas, preferably the removal of $NO_x$ from flue gases, $H_2S$ oxidation and metal extraction. Polyvalent metal chelates of the invention are particularly useful in removing $H_2S$ from a fluid, particularly a gas, containing $H_2S$, by (directly or indirectly) contacting the fluid with at least one chelate of at least one, preferably one polyvalent metal in a higher valence state such that sulfur is formed along with the chelate of the metal in a lower valence state. The chelate of any oxidizing polyvalent metal capable of being reduced by reaction with $H_2S$ or hydrosulfide and/or sulfide ions and, preferably which can be regenerated by oxidation, is suitable. Preferably the chelates are water soluble. Exemplary metals include lead, mercury, nickel, chromium, cobalt, tungsten, tin, vanadium, titanium, tantalum, platinum, palladium, zirconium, molybdenium, preferably iron, copper, or manganese, most preferably iron.

Chelates of the invention are suitably used in any process of removal of $H_2S$ within the skill in the art such as those exemplified by U.S. Pat. Nos. 4,421,733; 4,614,644; 4,629,608; 4,683,076; 4,696,802; 4,774,071; 4,816,238; and 4,830,838, which are incorporated by reference herein. The polyvalent metal chelates are readily formed in aqueous solution by reaction of an appropriate salt, oxide or hydroxide of the polyvalent metal and the chelating agent in the acid form or an alkali metal or ammonium salt thereof.

Preferably contact of $H_2S$, hydrosulfide, and/or sulfide with the chelate takes place at a pH of from about 6 to about 10. The more preferred range is from about 6.5 to about 9 and the most preferred range of pH is from about 7 to about 9. In general, operation at the highest portion of the range is preferred in order to operate at a high efficiency of hydrogen sulfide absorption. Since the hydrogen sulfide is an acid gas, there is a tendency for the hydrogen sulfide to lower the pH of the aqueous alkaline solution. Lower pH is preferable in the presence of carbon dioxide to reduce absorption thereof. Optimum pH also depends upon stability of a particular polyvalent metal chelate. At the pH values below about 6 the efficiency of hydrogen sulfide absorption is so low so as to be generally impractical. At pH values greater than 10, for instance with iron as the polyvalent metal, the precipitation of insoluble iron hydroxide may occur resulting in decomposition of the iron chelate. Those skilled in the art can ascertain a preferred pH for each operating situation.

Buffering agents optionally useful as components of aqueous alkaline scrubbing solutions of the invention include those which are capable of maintaining the aqueous alkaline solution at a pH generally in a operating pH range of about 6 to about 10. The buffering agents are advantageously water soluble at the concentration in which they are effective. Examples of suitable buffering agents include the ammonium or alkali metal salts of carbonates, bicarbonates, or borates, including sodium carbonate, bicarbonate or sodium borate, particularly carbonates and bicarbonates when used in the presence of $CO_2$ (carbon dioxide).

The temperatures employed in a contacting or absorption-contact zone are not generally critical, except that the reaction is carried out below the melting point of sulfur. In many commercial applications, absorption at ambient temperatures is desired. In general, temperatures from about 10° C. to about 80° C. are suitable, and temperatures from about 20° C. to about 45° C. are preferred. Contact times will range from about 1 second to about 270 seconds or longer, with contact times of 2 seconds to 120 seconds being preferred.

Pressure conditions suitably widely, depending on the pressure of the gas to be treated. For example, pressures in a contacting zone may vary from one atmosphere up to one hundred fifty or even two hundred atmospheres, with from one atmosphere to about one hundred atmospheres preferred.

In $H_2S$ removal, preferably at least an amount of chelate in a higher valence state stoichiomitric with the $H_2S$ to be removed is used. Preferred mole ratios of chelate to $H_2S$ are from about 1:1 to about 15:1, more preferably from about 2:1 to about 5:1. When chelates in both higher and lower valence states are present, it is generally preferable to maintain a concentration of lower valence state chelate at least about 5 times the concentration of that in the higher valence state. When, for instance an iron chelate is used, it is preferably present in an amount from about 100 to about 100,0000 ppm iron in the higher valence state most preferably from about 1000 to about 50,000 ppm by weight iron in the higher valence state. The circulation rate of the chelate solution depends upon the hydrogen sulfide level in the $H_2S$ containing fluid. In general, the circulation rate should be sufficient to provide from about 1 to about 6 moles and preferably about 2–4 moles of high valence (e.g. ferric) chelate for every mole of $H_2S$ entering the reaction zone. The contact time of the reactants should be at least about 0.05 second or more and preferably in the range from about 0.02 to about 1.0 seconds.

Chelates of the invention are preferably used in combination with additives such as rate enhancers (or catalysts, e.g. for conversion of $H_2S$ to sulfur) and/or stabilizers for the chelates. Cationic polymeric catalysts are advantageous and include polyethyleneamines, poly(2-hydroxypropyl-1-N-methylammonium chloride) and the 1,1-dimethyl analogue, poly[N-(dimethylaminomethyl) acrylamide], poly(2-vinylimidazolinum bisulfate), poly(diallyldimethyl ammonium chloride) and poly(N-dimethyl aminopropyl)-methacrylamide. These cationic polymers are well known and are commercially available under various tradenames. See, for example, Commercial Organic Flocculants by J. Vostrcil et al Noyes Data Corp. 1972 which is incorporated by reference herein. Other useful cationic catalysts are set forth in J. Macromol. Science-Chem. A4 pages 1327–1417 (1970) which is also incorporated by reference herein. Preferred catalysts include polyethylene amines and poly (diallyldimethyl ammonium chloride). Preferred concentration ranges for the polymeric catalysts are from about 0.75 to about 5.0 weight percent, and from about 1.0 to about 3.0 weight percent is the most preferred range. The amount of polymeric catalyst is sufficient to provide a weight ration of iron or other polyvalent metal in the range from 0.2 to 10:1. Concentrations of from about 10 to about 25 ppm in solution are preferred. Stabilizing agents include, e.g. bisulfite ions such as sodium, potassium, lithium, ammonium bisulfite and mixtures thereof. They are used in stabilizing amounts, ie. amounts sufficient to reduce or inhibit rate of degradation of the chelate, preferably from about 0.01 to about 0.6 equivalents per liter of solution, more preferably from about 0.05 to about 0.3 equivalents/liter.

After the chelate of lower valence state is produced from that of higher valence state, it is preferably oxidized back to the higher valence state and recycled. Oxidization is suitably by any means within the skill in the arty e.g. electrochemically, but preferably by contact with an oxygen-containing gas, e.g. air. If $CO_2$ is absorbed, it is preferably removed before contact with the oxygen-containing gas. The oxygen (in whatever form supplied) is advantageously supplied in a stoichiometric equivalent or excess with respect to the amount of lower valence state metal ion of the chelate or chelates present in the mixture. Preferably, the oxygen is supplied in an amount from about 1.2 to 3 time excess and in a concentration of from about 1 percent to about 100 percent by volume, more preferably from about 5 percent to about 25 percent by volume. Temperatures and pressures are suitably varied widely, but generally those used in the contacting zone(s) are preferred, preferably temperatures of from about 10° C. to about 80° C. more preferable from about 20° C. to about 45° C. with pressures from about 0.5 atmosphere to about 3 or 4 atmospheres preferred. Mild oxidizing conditions are generally preferred to avoid degradation of chelating agent. Such conditions are within the skill in the art.

Sulfur produced by reaction of $H_2S$ with the polyvalent metal chelate is optionally solubilized, e.g. by oxidation. Oxidation is suitably by any means within the skill in the art. When $SO_2$ is present or easily generated by oxidation of $H_2S$ (e.g. using oxygen or electrochemical means) it is a preferred oxidizing agent to produce, e.g. thiosulfates from the sulfur. Other suitable oxidizing agents include e.g. alkali metal or ammonium salts of inorganic oxidizing acids such as perchloric, chloric, hypochlorous, and permanganic acids. Otherwise, the sulfur is optionally recovered by means within the skill in the art including flocculation, settling, centrifugation, filtration, flotation and the like.

Processes of the invention include, for instance: a process for removing at least a portion of $H_2S$ from a fluid stream containing $H_2S$ which comprises (A) contacting said fluid stream (optionally in a first reaction zone) with an aqueous solution at a pH range suitable for removing $H_2S$ wherein said solution comprises at least one higher valence polyvalent metal chelate of Formula I whereby said higher valence polyvalent metal chelate is reduced to a lower valence polyvalent metal chelate. Optionally the aqueous solution additionally comprises an oxidizing agent capable of oxidizing elemental sulfur to soluble sulfur compounds, and/or one or more water soluble cationic polymeric catalysts and/or a stabilizing amount of a stabilizing agent each as bisulfite ion.

The process optionally includes at least one additional step such as:

(B) contacting said solution containing the lower valence polyvalent chelate in a second reaction zone with an oxygen-containing gas stream whereby said chelate is reoxidized;

(C) recirculating said reoxidized solution back to said first reaction zone;

(D) feeding said aqueous solution from said oxidation zone to a sulfur recovery zone;

(E) removing from said aqueous solution at least a portion of said sulfur and thereafter;

(F) regenerating the aqueous admixture in a regeneration zone to produce a regenerated reactant;

(G) returning aqueous admixture containing regenerated reactant from the regeneration zone to the contacting zone;

(H) incinerating hydrogen sulfide to form sulfur dioxide;

(I) selectively absorbing said sulfur dioxide in an alkaline aqueous solution without substantial carbon dioxide absorption to form a solution of sulfites essentially free of insoluble carbonates;

(J) contacting said sulfur with said sulfites to form soluble sulfur compounds;

(K) recirculating said reoxidized polyvalent metal chelate back to said fluid stream/aqueous chelate solution contacting step; and/or (L) condensing geothermal steam in a reaction zone, preferably in said first reaction zone, for contacting said reduced polyvalent metal chelate.

Compositions of the invention, thus, include aqueous solutions of polyvalent metal chelates of the invention (in one or more oxidation states) with at least one of: $H_2S$, sulfide or bisulfide ions, rate enhancers such as poly(dimethyldiallyl ammonium chloride) and/or polyethyleneamines, and/or stabilizers such as bisulfite ions.

Similarly, chelates of the invention are used in removal of nitrogen oxides, preferably nitric oxide (NO), from fluids containing them. For instance, nitrogen oxides ($NO_X$) and $SO_2$ can be removed from flue gas streams by absorbing the $SO_2$ using an absorbent or reactant therefor, particularly an amine based absorbent such as a nitrogen-containing heterocyclic compound preferably having at least one carbonyl group such as a piperazinone; piperidinone, piperidine, piperazine or triazine having a carbonyl group; hydantoin; cyclic urea, oxazolidone or morpholinone in conjunction with a chelate of a polyvalent metal. Representative metal ions are chromium, cobalt, copper, iron, lead, manganese, mercury, molydenum, nickel, palladium, platinum tin, titanium, tungsten, and vandium; preferably iron, copper, and/or nickel all preferably with a valence of +2, the more preferably iron, most preferably iron in the ferrous state. Such chelates are conveniently prepared by admixing a water soluble salt of the metal, such as a sulfate, acetate, or oxalate, with a water soluble form of the chelating agent, e.g. a salt, advantageously in water. The chelates are useful in any process within the skill in the art such as those disclosed in U.S. Pat. Nos. 4,732,744 to Chang et al.; 4,612,175 to Harkness et al.; 4,708,854 to Grinstead; 4,615,780 to Walker; 4,126,529 to DeBerry; 4,820,391 to Walker; and 4,957,716 to Cichanowicz et al. When an $SO_2$ absorbent is used, it is preferably regenerated, more preferably thermally regenerated, and preferably recycled. The concentration of $NO_X$ in the fluid (directly or indirectly) contacting the chelate is preferably from about 1 ppm to about 15,000 ppm by volume such as is found, for instance, in flue gases from burning e.g. coal.

Whether used with an absorbent for $SO_2$ or not, the metal chelate is advantageously present in the solution which contacts the $NO_X$ containing fluid at a metal ion concentration greater than about 100 ppm with a chelating agent to metal ion molecular ratio of greater than or equal to one. The metal chelate is preferably present at a metal ion concentration of about 1,000 to about 10,000 ppm and a chelating agent to metal ion molecular ratio between about 1:1 and about 10:1. The optimum amounts depend on the chelating agent generally with preferred ratios between about 1:1 and to about 5:1.

An absorber is suitably operated at a temperature of from about 0° to about 120° C., but is preferably operated at a temperature of from about 5° to about 95° C. In the process, both absorber and (optionally) a stripper are typically operated at a pressure of from about atmospheric to about 10 atmospheres (e.g. 0 to about 69 Pa gauge), however, atmospheric pressure is preferred for the convenience of lower equipment and operating costs and reduced $SO_2$ absorbent losses. Higher temperatures and pressures are not deleterious so long as they are below the decomposition temperature of the chelate and absorbent, if present. The absorber is preferably maintained at a pH between about 3 and about 8 to retain $NO_x$ absorbence in the absorber.

Chelates absorb $NO_x$ or act as stoichiometric reactants to increase the solubility of $NO_x$ in aqueous solution. Preferably sulfite and/or bisulfite ions collectively referred to herein as "sulfites" are also present. Such ions react with the $NO_X$-chelate complex to form iminodisulfonate salts and free the chelate for $NO_x$ absorption. Examples of suitable soluble sulfite salts include sodium, potassium, lithium, magnesium and/or ammonium sulfite and/or bisulfite. When $SO_2$ is present, $SO_2$ in aqueous solution forms sulfurous acid, and the concentration of sulfites in the absorbent is generally sufficient for iminodisulfonate formation without replenishment, but sulfites may be added, if necessary, to maintain a concentration of at least 0.05 to about 1 g-moles/l absorbent, preferably at least about 0.1 g-moles/l. A sulfite salt is, thus, preferably present with the chelate.

Alternatively, as described in U.S. Pat. No. 4,957,716, which is incorporated herein by reference in its entirety, the chelate promotes absorption of $NO_X$ which may be converted to such compounds as $HNO_2$ and $HNO_3$ which react with $HSO_3$, if present, to form hydroxylamine-disulfonate ($HON(SO_3H)_2$, abbreviated HADS) and related compounds, which are preferably subsequently converted to soluble ammonium and sulfate ions advantageously at a pH of about 4.2 or less, preferably about 4. More preferably the ammonium ions are subsequently removed, e.g. by absorption, and most preferably, the sulfate ions are precipitated.

In removing $NO_X$ from a fluid, the polyvalent metal chelate is oxidized from a lower to a higher valence state. The lower valence metal chelate is preferably replenished, e.g. by replacement of the polyvalent metal ion of the chelate, but more preferably by reduction of the metal by any means within the skill in the art, such as contact with a reducing agent, or by acidification e.g. by reducing the pH below about 4.2 using an acid such as sulfuric acid, or preferably by electrochemical means (at a cathode). The chelate is, then, preferably recycled.

When electrochemical regeneration is used, the solution containing the higher valence polyvalent metal chelate (which solution is preferably first (advantageously thermally) stripped of $SO_2$) is preferably directed to a cathode compartment of an electrochemical cell comprised of an anode in an anode compartment separated, preferably by a membrane, from a cathode in a cathode compartment. An electrical potential is imposed across the anode and cathode to reduce inactive oxidized chelates to an active state. Preferably, an anionic exchange membrane is used. Heat stable amine salts may also be converted to free amine sorbent in the cathode compartment and soluble salt anions diffuse from the cathode compartment through the anion exchange membrane into the anode department. Preferably, in a further step, regenerated absorbent solution from the cathode compartment is recycled to the $NO_x$ containing fluid contacting step. The process more preferably additionally comprises a step of adjusting the pH of the regenerated recycle absorbent to from about 3 to about 8.

Compositions of the invention, thus, include aqueous solutions of the polyvalent metal chelates of the invention with at least one of $NO_X$, at least one (water soluble) sulfite, or at least one absorbent for $SO_2$. Mixtures of the chelates in higher and lower valence states and mixtures of the chelate with the chelate —$NO_X$ complex are also aspects of the instant invention.

Processes of the invention, thus, include a process for removing at least a portion of $NO_X$, preferably NO, from a fluid containing $NO_X$, said fluid preferably also containing $SO_2$ and said fluid preferably being a gas, but suitably being a liquid, suspension, condensate and the like comprising the step of (A) (directly or indirectly) contacting the fluid with an aqueous solution comprising at least one lower valence state polyvalent metal chelate of the invention and optionally additionally containing an absorbent for $SO_2$ and/or a sulfite.

The process optionally additionally comprises at least one of the following steps:

(B) thermally stripping sulfur dioxide from an $SO_2$-rich absorbent solution to obtain an $SO_2$-lean absorbent solution;

(C) directing the absorbent solution to a cathode compartment in an electrochemical cell, said cell having an anode in an anode compartment separated (preferably by a membrane) from a cathode in said cathode compartment, and imposing an electrical potential across said anode and said cathode to reduce oxidized chelates in said cathode compartment to obtain a regenerated absorbent solution;

(D) recycling said regenerated absorbent solution to contacting step (A);

(E) converting heat stable amine salts into free amine absorbent in said cathode compartment;

(F) separating salt anions from said cathode compartment through said anionic exchange membrane into said anode compartment;

(G) circulating an aqueous electrolyte solution through said anode compartment;

(H) periodically refreshing said electrolyte to eliminate byproduct salts in said anode compartment;

(I) adjusting said regenerated absorbent solution to a pH of from about 3 to about 8 for a recycling step;

(J) (when HADS is formed) mixing at least a portion of hydroxylaminedisulfonate in a reaction zone in an aqueous environment of pH of 4.2 or less, thereby converting said hydroxylaminedisulfonate to ammonium ions and sulfate ions in a second aqueous solution;

(K) contacting said second aqueous solution with a second ammonium ion-absorbing sorbent suitable for removing ammonium ions from said second aqueous solution and separating said second sorbent from said second aqueous solution;

(L) eluting said second sorbent and exposing the eluted ammonium ions or ammonia to nitrogen oxides at a temperature sufficient to form nitrogen and water therefrom; and/or (M) removing said sulfate ions from said second aqueous solution by forming a sulfate salt precipitate.

The chelants for alkaline earth metal and heavy metal ions according to the invention are used as complexing agents in general and specifically in detergents and also rinse and wash assistants, in particular as complexing agents for heavy metal and/or alkaline earth metal ions, as bleaching agent stabilizers and as builders.

The present invention accordingly provides the corresponding uses and detergents which contain these compounds as well as the constituents known to those skilled in the art.

The compounds to be used according to the invention are used in cleaning formulations, particularly detergent, in general in an amount from about 0.01 to about 40 weight percent, preferably from about 0.05 to about 20 weight percent, more preferably from about 0.1 to about 10 weight percent based on the total weight of the detergent formulation.

If specifically used as a builder, amounts from about 1 to about 40 percent by weight are particularly preferred, while if specifically used as a bleaching agent stabilizer for perborates, or other bleaches such as sources of hydrogen peroxide or oxygen including percarbonates, peroxides (e.g. hydrogen peroxide or sodium peroxide), persulfate, perthalates, per acid precursors (e.g. tetraacetyl-ethylene diamine) and the like, amounts from about 0.05 to about 1 percent by weight are preferred. If used specifically as a chelant in detergents, amounts from about 0.01 to about 2 percent by weight are preferred. Chelants of the invention are particularly useful in stabilizing bleach, particularly peroxide bleaches, more particularly perborates.

As builders, the chelants of this invention can be advantageously used with a wide variety of detergent actives or surfactants, including those known in the art as anionic, cationic, nonionic, ampholytic, and zwitterionic detergents as well as any suitable mixture of such detergents. When the resultant washing compositions are used in aqueous washing systems, the cleaning power of the formulation is enhanced in much the same way as when the commonly used polyphosphate builders are employed. Yet the present builder systems are more favorably degraded than the polyphosphates and do not contribute to the eutrophication problems characteristic of phosphorus-containing builders.

Accordingly, this invention provides, inter alia, a washing composition composed of an organic detergent surfactant suitable for use in water and, as a builder, a water-soluble salt of at least one acid of Formula I. Although the proportions may be varied to suit the needs of the occasion, the weight ratio of the detergent surfactant to the builder of this invention will normally fall within the range of about 100:1 to about 1:10.

For best results, the formulations of this invention wherein compounds of the invention are used as builders will provide in aqueous solution a pH between about 8 and about 12.

Detergent formulations which, based on the total weight, contain from about 0.01 to about 40, preferably from about 0.05 to about 20 percent by weight of compound to be used according to the invention generally contain as additional constituents, based on the total weight, from about 6 to about 25 percent by weight of surfactants, from about 15 to about 50 percent by weight of builders with or without cobuilders, from about 0 to about 35 percent by weight of bleaching agents with or without bleaching agent activators, and from about 3 to about 30 percent by weight of assistants, such as enzymes, foam regulants, corrosion inhibitors, optical brighteners, scents, dyes or formulation aids, eg. sodium sulfate.

The compounds of this invention can be used with a wide variety of detergents including those classed in the art as anionic detergents, cationic detergents, nonionic detergents, ampholytic (i.e., amphoteric) detergents, and zwitterionic detergents, and any suitable mixture of two or more of these (whether from the same class or from different classes). The chelants of this invention perform particularly well with anionic or nonionic surface-active compounds and therefore this constitutes a preferred embodiment of the invention.

Another preferred embodiment of this invention is a washing composition comprising an organic detergent surfactant, at least one water-soluble salt of an acid of Formula 1 and about 2 to about 10 percent by weight based on the total weight of the composition of a water-soluble alkali metal silicate. The cleaning efficiency of these preferred compositions is at least comparable to commercially available household and laundry formulations. Moreover, the soluble silicates of such alkali metals as sodium and potassium serve as effective corrosion inhibitors. In accordance with this preferred embodiment it is desirable to employ one or more silicates of sodium or potassium, or both, wherein the weight ratio of $SiO_2$: $M_2O$ (M=Na or K) is in the range of from about 1:1 to about 2.8:1. Sodium silicates wherein this ratio is in the range of from about 1.6:1 to about 2.5:1 are especially useful because of their low cost and effectiveness.

Another preferred embodiment of this invention involves including with the mixture of the organic detergent surfactant and the compounds of the invention (e.g., the tetrasodium salt, the tetrapotassium salt, or the mixed sodium-potassium salts-including the partial and complete salts thereof), an alkali metal sulfate, preferably sodium sulfate, or an alkali metal carbonate, preferably sodium carbonate, or both. Amounts of the compounds of the invention up to about 60 percent by weight of the total formulation are suitable. These formulations are effective detergent formulations for laundry, household and/or industrial use. In the preferred compositions the amount of alkali metal sulfate and/or alkali metal carbonate is generally from about 10 to about 50 percent by weight based on the total weight of the formulation.

In a particularly preferred embodiment, compounds of Formula I (chelants) are used with surfactants in compositions additionally containing a bleaching agent, preferably a bleaching agent which supplies a peroxide ion in water such as hydrogen peroxide, a perborate salt, percarbonate salt or shelf-stable form of peroxide, more preferably the bleaching agent is a perborate salt or hydrogen peroxide, most preferably the bleaching agent is sodium perborate or hydrogen peroxide (in aqueous solution). While the chelants are present in a weight ratio of from about 1:40 to about 10:1, preferably from about 1:5 to about 3:2 relative to the surfactant; the bleaching agent is present in a ratio of from about 150:1 to about 2:1, preferably from about 60:1 to about 20:1 relative to the bleach stabilizer; in a solution containing bleaching agent, the bleaching agent is advantageously present in an amount of from about 2 to about 50, preferably from about 10 to about 30 weight percent based on dry detergent formulation. In bleaching compositions having little or no surfactant, such as those for all fabric bleaches or peroxy bleach additives, the chelants are preferably present in amount of from about 0.05 to about 5 percent by weight relative to the bleaching agent present.

Compounds of the invention are also advantageously used in cleaning compositions, particularly laundry compositions, having low phosphate. For instance, a typical dry phosphate detergent composition would have from about 5 to about 50 percent phosphate and from 0 to about 10 by weight chelant. Chelants of the invention are preferably used in compositions having less than about 40 weight percent phosphate, more preferably less than about 30, most preferably less than about 20, even more preferably less than about 10 weight percent phosphate. Such compositions preferably contain from about 0.2 to about 20 weight percent chelant, more preferably from 0.5 to about 5 by weight chelant.

Chelants of the invention are also useful in surfactant-free cleaning compositions including built cleaning compositions suitable for hard-surface cleaning, such as certain automatic dishwashing agents and kitchen or bathroom cleaners. Such cleaning compositions generally comprise from about 1 percent to about 99.95 percent, preferably about 90 percent to about 99 weight percent, of a conventional builder and at least about 0.5 weight percent, typically about 0.1 to about 5 weight percent chelant.

Hard surface cleaners preferably include at least one organic solvent with the chelant and, more preferably also contain at least one builder and/or surfactant. The use of builders which are primarily polyphosphates or nitrogenous chelants like NTA with terpenes, benzyl alcohol or butyl carbinol are discussed in European Patent Applications 40,882; 80,749 and 126,545. The use of glycol ether derivatives as solvents are discussed in European Patent Application 105,863 and U.S. Pat. No. 3,591,510. More recently, it was noted that solvents preferably have a boiling point of at least about 90° C. (See European Patent Applications 317,542 and 513,948 and U.S. Pat. No. 5,202,050 which is incorporated herein by reference in its entirety.) Use of solvents having a boiling point of at least about 90° C. results in improved soil-release benefits from the chelate-solvent composition, especially in the removal of calcium soap-soil from surfaces such as bathtub surfaces.

Representative organic solvents effective in the present invention are: $C_6$–$C_9$ alkyl aromatic solvents, especially the $C_6$–$C_9$ alkyl benzenes, alphaolefins, like 1-decene or 1-dodecene, benzyl alcohol, n-hexanol, phthalic acid esters or combination thereof $C_1$–$C_3$ aliphatic alcohols like isopropanol (B.P. 82° C.) are less effective.

Among solvents particularly useful in the hard surface cleaning compositions of the invention are diols having from about 6 to about 16, preferably about 8 to about 12, carbon atoms in their molecular structure. Preferred diol solvents have a solubility in water of from about 0.1 to about 20 g/100 g of water at 20° C. The most preferred diol solvents are 2,2,4-trimethyl-1,3-pentanediol, and 2-ethyl-1,3-hexanediol.

Glycol ethers are among the preferred solvents. Such glycol ethers include: water-soluble CARBITOL solvents or water-soluble CELLOSOLVE solvents commercially available from Union Carbide Corp. Water soluble CARBITOL solvents are compounds of the 2-(2-alkoxyethoxy) ethanol class wherein the alkoxy group is preferably derived from ethyl, propyl, butyl, pentyl, or hexyl. A preferred water-soluble carbitol is 2-(2-butoxyethoxy) ethanol also known as butyl carbitol. Preferred are also hexyl carbitol and 2-methyl pentyl carbitol. Water-soluble CELLOSOLVE solvents are compounds of the 2-alkoxyethoxy ethanol class, wherein the alkoxy group is preferably butyl or hexyl. Other glycol ethers include certain propylene-glycol derivatives including especially 1-n-butoxypropane-2-ol, and 1 (2-n-butoxy-1-methylethoxy) propane-2-ol (butoxypropoxypropanol), with the latter being especially preferred.

Mixtures of the above solvents are also suitably used for instance, butyl carbitol and/or benzyl alcohol is useful combined with diols and/or glycol ethers.

The organic solvent is preferably present at level of from about 1 percent to about 20 percent by weight of the total composition, preferably from about 1 percent to about 10 percent. The weight ratio of organic solvent to chelating agent is preferably in the range from about 2/3 to about 2/1, preferably about 1/1 to about 2/1 to achieve more desirable effects in calcium soap-soil removal.

In the present invention, use of chelants of Formula I with the solvents in hard surface cleaners has a major advantage of biodegradability of the chelant.

Additives within the skill in the art of hard surface cleaners are also optionally present. For instance surface-active agents are beneficial. Such surface active agents include water-soluble surfactants such as synthetic anionic, nonionic, cationic, amphoteric and zwitterionic surfactants and mixtures thereof. Exemplary surfactants include the alkyl benzene sulfates and sulfonates, paraffin sulfonates, olefin sulfonates, alkoxylated (especially ethoxylated) alcohols and alkyl phenols, amine oxides, sulfonates of fatty acids and of fatty acid esters, and the like, which are known in the detergency art. Preferably, such surfactants contain an alkyl group in about the $C_{10}$–$C_{18}$ range. Anionic surfactants are commonly used in the form of their sodium, potassium or triethanolammonium salts. The nonionics advantageously contain from about 3 to about 17 ethylene oxide groups per mole of hydrophobic moiety. Representative cationic surfactants include quaternary ammonium compounds such as ditallow dimethyl ammonium chloride, and are preferably used in combination with nonionic surfactants about $C_{12}$–$C_{16}$ alkyl benzene sulfonates, about $C_{12}$–$C_{18}$ paraffin-sulfonates and the ethoxylated alcohols of the formula $RO(CH_2-CH_2O)n$, with R being a $C_{12}$–$C_{15}$ alkyl chain and n being a number from 6 to 10, and the ethoxylated alcohol sulfates of formula $RO-(CH_2-CH_2O)n-SO_3M$, with R being a $C_{12}$–$C_{18}$ alkyl chain n a number from about 2 to about 8, and M is H or an alkali metal ion.

Anionic surfactants are advantageously present at levels from about 0.3 percent to about 8 percent of the hard surface cleaning composition. Nonionic surfactants, are preferably used at levels between about 0.1 percent to about 6 percent by weight of the composition. Mixtures of surfactants are also useful.

Other optional ingredients include detergent builders within the skill in the art, including the nitrilotriacetates (NTA), polycarboxylates, citrates, water-soluble phosphates such as tri-polyphosphate and sodium ortho- and pyro-phosphates, silicates, ethylene diamine tetraacetate (EDTA), amino-polyphosphonates (DEQUEST), phosphates and mixtures thereof.

Other optional, and preferred, additives for the hard surface cleaners include detergent hydrotropes. Exemplary hydrotropes include urea, monoethanolamine, diethanolamine, triethanolamine and the sodium potassium, ammonium and alkanol ammonium salts of xylene-, toluene-, ethylbenzene- and isopropyl-benzene sulfonates.

The hard-surface clearing compositions of the invention also optionally contain an abrasive material. The abrasive materials include water-insoluble, non-gritty materials known for their relatively mild abrasive properties. It is preferred that the abrasives used herein not be undesirably "scratchy". Abrasive materials having a Mohs hardness in no more than about 7 are preferred; while abrasives having a Mohs hardness of no more than about 3, are useful to avoid scratches on finishes such as aluminum or stainless steel. Suitable abrasives include inorganic materials, especially such materials as calcium carbonate and diatomaceous earth, as well as materials such as Fuller's earth, magnesium carbonate, China clay, actapulgite, calcium hydroxyapatite, calcium orthophosphate, dolomite and the like. The aforesaid inorganic materials can be described as "strong abrasives". Organic abrasives such as urea-formaldehyde, methyl methacrylate melamine-formaldehyde resins, polyethylene sphere and polyvinylchloride are advantageously used to avoid scratching on certain more delicate surfaces, such as plastic surfaces. Preferred abrasives have a particle size range of about 10–1000 microns and are preferably used at concentrations of about 5 percent to about 30 weight percent of the hard surface cleaning compositions.

Thickeners are preferably used to suspend the abrasives. Levels of thickener difficult to rinse from the cleaned surfaces are undesirable. Accordingly, the level is preferably less than about 2 percent, preferably from about 0.25 to about 1.5 percent. Exemplary thickeners include polyacrylates, xanthan gums, carboxymethyl celluloses, swellable smectite clay, and the like.

Soaps, especially soaps prepared from coconut oil fatty acids are also optionally included in the hard surface cleaners.

Optional components include components within the skill in the art to provide aesthetic or additional product performance benefits. Such components include perfumes, dyes, optical brighteners, soil suspending agents, detersive enzymes, gel-control agents, thickeners, freeze-thaw stabilizers, bactericides, preservatives, and the like.

The hard-surface cleaning compositions of the invention are advantageously in the form of liquid compositions, preferably aqueous compositions, including concentrates, containing as essential ingredients the solvent and chelating agent of Formula I. Preferably a surfactant is also present, more preferably in a concentration that corresponds to from about 2 to about 6 percent surfactant to from about 8 to about 12 percent by weight solvent/chelating agent mixture. Concentrated liquid compositions preferably contain from about 6 to about 10 percent surfactant and from about 16 to about 24 percent solvent/chelating agent mixture.

Alternatively, the compositions herein are in the form of creamy scouring cleansers, preferably containing an abrasive material, surface-active agent, and the solvent/chelating agent mixture of the invention.

Most preferably, whether in liquid, creamy or other form, the hard surface cleaning compositions have a neutral or alkaline pH, preferably in the range of from about 5 to about 11.

The compounds according to the invention can also be used as complexing agents, builders and bleaching agent stabilizers in detergent formulations together with other, prior art agents, in which case the general properties can be substantially improved in respect of sequestration, incrustation inhibition, grayness inhibition, primary washing action and bleaching action.

Suitable surfactants for use in the cleaning compositions of the invention are those which contain in the molecule one or more hydrophobic organic radicals and one or more water-solubilizing anionic, zwitterionic or nonionic groups. The hydrophobic radicals usually are aliphatic hydrocarbyl of 8 to 26, preferably 10 to 22, in particular 12 to 18, carbon atoms or aromatic alkyl having 6 to 18, preferably 8 to 16, aliphatic carbon atoms.

Suitable synthetic anionic surfactants are in particular those of the sulfonate, sulfate or synthetic carboxylate type.

Suitable builder substances are for example: wash alkalis, such as sodium carbonate and sodium silicate, or complexing agents, such as phosphates, or ion exchangers, such as zeolites, and mixtures thereof. These builder substances have as their function to eliminate the hardness ions, which come partialy from the water, partialy from dirt or textile material, and to support the surfactant action. In addition to the abovementioned builder substances, the builder component may further contain cobuilders. In modern detergents, it is the function of cobuilders to undertake some of the functions of phosphates, eg. sequestration, soil antiredepositon and primary and secondary washing action.

The builder components may contain for example water-insoluble silicates as described for example in German Laid-Open Application DE-OS No. 2,412,837 and/or phosphates. As phosphate it is possible to use pyrophosphates, triphosphates, higher polyphosphates and metaphophates. Similarly, phosphorus-containing organic complexing agents such as alkanepolyphosphonic acids, amino- and hydroxy-alkanepolyphosphonic acids and phosphonocarboxylic acids, are suitable for use as further detergent ingredients generally referred to as stabilizers or phosphonates. Examples of such detergent additives are the following compounds: methanediphophonic acid, propane-1,2,3-triphosphonic acid, butane-1,2,3,4-tetraphosphonic acid, polyvinylphosphonic acid, 1-aminoethane,-1,1-diphosphonic acid, aminotrismethylenetriphosphonic acid, methylamino- or ethylamino-bismethylenediphosphonic acid, ethylenediaminetetramethylenetraphosphonic acid, diethylenetriaminopentamethylenepentaphosphonic acid, 1-hydroxyethane-1,1-diphosphonic acid, phosphonoacetic and phosphonopropionic acid, copolymers of vinylphosphonic acid and acrylic and/or maleic acid and also partially or completely neutralized salts thereof.

Further organic compounds which act as chelants for calcium and may be present in detergent formulations are polycarboxylic acids, hydroxcarboxylic acids and aminocarboxylic acids which are usually used in the form of their water-soluble salts.

Examples of polycarboxylic acids are dicarboxylic acids of the general formula $HOOC\text{-}(CH_2)_m\text{-}COOH$ where m is 0–8, and also maleic acid, methylenemalonic acid, citraconic acids mesaconic acid, itaconic acid, noncyclic polycarboxylic acids having 3 or more carboxyl groups in the molecule, e.g. tricarballylic acid, aconitic acid, ethylenetetracarboxylic acid, 1,1,3-propanetetracarboxylic acid, 1,1,3,3,5,5-pentanehexacarboxylic acid, hexanehexacarboxylic acid, cyclic di- or poly-carboxylic acids, e.g. cyclopentanetetracarboxylic acid, cyclohexanehexacarboxylic acid, tetrahydrofurantetracarboxylic acid, phthalic acid, terephthalic acid, benzene-tricarboxylic, -tetracarboxylic or -pentacarboxylic acid and mellitic acid.

Examples of hydroxymonocarboxylic and hydroxypolycarboxylic acids are glycollic acid, lactic acid, malic acid, tartronic acid, methyltartronic acid, gluconic acid, glyceric acid, citric acid, tartaric acid and salicylic acid.

Examples of aminocarboxylic acids are glycine, glycylglycine, alanine, asparagine, glutamic acid, aminobenzoic acid, iminodiacetic acid, iminotriacetic acid, hydroxyethyliminodiacetic acid, ethylenediaminetetraacetic acid, hydroxyethylethylenediaminetriacetic acid, diethylenetriaminepentaacetic acid and higher homologues which are preparable by polymerization of an N-aziridylcarboxylic acid derivative, for example of acetic acid, succinic acid or tricarballylic acid, and subsequent hydrolysis, or by condensation of polyamines having a molecular weight of from 500 to 10,000 with salts of chloroacetic or bromoacetic acid.

Preferred cobuilder substances are polymeric carboxylates. These polymeric carboxylic acids shall include the carboxymethyl ethers of sugars, of starch and of cellulose. Zeolites and phosphates are also useful.

Particularly important polymeric carboxylic acids are for example the polymers of acrylic acid, maleic acid, itaconic acid, mesaconic acid, aconitic acid, methylenemalonic acid, citraconic acid and the like, the copolymers between the aforementioned carboxylic acids, for example a copolymer of acrylic acid and maleic acid in a ration of 70:30 and having a molecular weight of 70,000, or copolymers thereof with ethylenically unsaturated compounds, such as ethylene, propylene, isobutylene, vinyl methyl ether, furan, acrolein, vinyl acetate, acrylamide, acrylonitrile methacrylic acid, crotonic acid and the like, e.g. the 1:1 copolymers of maleic anhydride and methyl vinyl ether having a molecular weight of 70,000 or the copolymers of maleic anhydride and ethylene and/or propylene and/or furan.

The cobuilders may further contain soil antiredeposition agents which keep the dirt detached from the fiber in suspension in the liquid and thus inhibit graying. Suitable for this purpose are water-soluble colloids usually of an organic nature for example the water-soluble salts of polymeric carboxylic acids, glue, gelatin, salts of ethercarboxylic acids or ethersulfonic acids of starch and of cellulose or salts of acid sulfates of cellulose and of starch. Even water-soluble polyamides containing acid groups are suitable for this purpose. It is also possible to use soluble starch products and starch products other than those mentioned above, for example degraded starch, aidehyde starches and the like. Polyvinylpyrrolidone is also usable.

Bleaching agents are in particular hydrogen peroxide and derivatives thereof or available chlorine compounds. Of the bleaching agent compounds which provide $H_2O_2$ in water, sodium perborate hydrates, such as $NaBO_2.H_2O_2.3H_2O$ and $NaBO_2.H_2O_2$, are particular importance. However, it is also possible to use other $H_2O_2$-providing borates. These compounds can be replaced in part or in full by other sources of active oxygen, in particular by peroxyhydrates, such as peroxycarbonates, peroxyphosphonates, citrate perhydrates, urea-$H_2O_2$-providing peracid salts, for example caroates, perbenzoates or peroxyphthalates or other peroxy compounds.

Aside from those according to the invention, customary water-soluble and/or water-insoluble stabilizers for peroxy compounds can be incorporated together with the former in amounts from 0.25 to 10 percent by weight, based on the peroxy compound. Suitable water-insoluble stabilizers are the magnesium silicates $MgO:SiO_2$ from 4:1 to 1:4, preferably from 2:1 to 1:2, in particular 1:1, in composition, usually obtained by precipitation from aqueous solutions. Other alkaline earth metals of corresponding composition are also suitably used.

To obtain a satisfactory bleaching action even in washing at below 80° C., in particular in the range from 60° C. to 40° C., it is advantageous to incorporate bleach activators in the detergent, advantageously in an amount from 5 to 30 percent by weight, based on the $H_2O_2$-providing compound.

Activators for per-compounds which provide $H_2O_2$ in water are certain N-acyl and O-acyl compounds, in particular acetyl, propionyl or benzyl compounds, which form organic peracids with $H_2O_2$ and also carbonic and pyrocarbonic esters. Useful compounds are inter alia:

N-diacylated and N,N'-tetraacylated amines, e.g. N,N,N',N'-tetraacetyl-methylenediamine or ethylenediamine, N,N-diacetylaniline and N,N-diacetyl-p-toluidine, and 1,3-diacylated hydantoins, alkyl-N-sulfonylcarboxamides, N-acylated hydrazides, acylated triazoles or urazoles, e.g. monoacetylmaleohydrazide, O,N,N-trisubstituted hydroxylamines, e.g. O-benzoyl-N,N-succinylhydroxylamine, O-acetyl-N,N-succinylhydroxylamine, O-p-methoxybenzoyl-N,N-succinylhydroxylamine, O-p-nitrobenzoyl-N,N-succinylhydroxylamine and O,N,N-triacetylhydroxylamine, carboxylic anhydrides, e.g. benzoic anhydride, m-chlorobenzoic anhydride, phthalic anhydride and 4-chlorophthalic anhydride, sugar esters, e.g. glucose pentaacetate, imidazolidine derivatives, such as 1,3-diformyl -4,5-diacetoxyimidazolidine, 1,3-diacetyl-4,5-diacetoxyimidazoline and 1,3-diacetyl-4,5-dipropionyloxyimidazolidine, acylated glycolurils, e.g. tetrapropionylglycoluril or diacetyldibenzoylglycoluril, dialkylated 2,5-diketopiperazines, e.g. 1,4-dipropionyl-2,5-diketopiperazine and 1,4-dipropionyl-3,6-dimethyl-2,5-diketopiperazine and 1,4-dipropionyl-3,6-2,5-diketopiperazine, acetylation and benzoylation products of propylenediurea or 2,2-dimethylpropylenediurea.

The sodium salt of p-(ethoxycarbonyloxy)benzoic acid and of p-(propoxycarbonyloxy) benzenesulfonic acid and also the sodium salts of alkylated or acylated phenolsulfonic esters, such as p-acetoxybenzenesulfonic acid, 2-acetoxy-5-nonylbenzenesulfonic acid, 2-acetoxy-5-propylbenzenesulfonic acid or of isononanoyloxyphenylsulfonic acid.

The bleaching agents used can also be active chlorine compounds of the inorganic or organic type. Inorganic active chlorine compounds include alkali metal hypochlorites which can be used in particular in the form of their mixed salts and adducts on orthophosphates or condensed phosphates, for example on pyrophosphates and polyphosphates or on alkali metal silicates. If the detergent contains monopersulfates and chlorides, active chlorine will form in aqueous solution.

Organic active chlorine compounds are in particular the N-chlorine compounds where one or two chlorine atoms are bonded to a nitrogen atom and where preferably the third valence of the nitrogen atom leads to a negative group, in particular to a CO or $SO_2$ group. These compounds include dichlorocyanuric and trichlorocyanuric acid and their salts, chlorinated alkylguanides or alkylbiguanides, chlorinated hydantoins and chlorinated melamines.

Examples of additional assistants are: suitable foam regulants, in particular if surfactants of the sulfonate or sulfate type are used, are surface-active carboxybetaines or sulfobetaines and also the abovementioned nonionics of the alkylolamide type. Also suitable for this purpose are fatty alcohols or higher terminal diols.

Reduced foaming, which is desirable in particular for machine washing, is frequently obtained by combining various types of surfactants, for example sulfates and/or sulfonates, with nonionics and/or with soaps. In the case of soaps, the foam inhibition increases with the degree of saturation and the number of carbon atoms of the fatty acid ester; soaps of saturated $C_{20}$–$C_{24}$-fatty acids, therefore, are particularly suitable for use as foam inhibitors.

The nonsurfactant-like foam inhibitors include optionally chlorine-containing N-alkylated aminotriazines which are obtained by reacting 1 mole of cyanuric chloride with from 2 to 3 moles of a mono- and/or dialkylamine having 6 to 20, preferably 8 to 18, carbon atoms in the alkyl. A similar effect is possessed by propoxylated and/or butoxylated aminotriazines, for example, products obtained by addition of from 5 to 10 moles of propylene oxide onto 1 mole of melamine and further addition of from 10 to 50 moles of butylene oxide onto this propylene oxide derivative.

Other suitable nonsurfactant-like foam inhibitors are water-soluble organic compounds, such as paraffins or haloparaffins having melting points below 100° C., aliphatic $C_{18}$- to $C_{40}$-ketones and also aliphatic carboxylic esters which, in the acid or in the alcohol moiety, possibly even both these moieties, contain not less than 18 carbon atoms (for example triglycerides or fatty acid fatty alcohol esters); they can be used in particular in combinations of surfactants of the sulfate and/or sulfonate type with soaps for foam inhibition.

The detergents may contain optical brighteners for cotton, for polyamide, for polyacrylonitrile or for polyester fabrics. Examples of suitable optical brighteners are derivatives of diaminostilbenedisulfonic acid for cotton, derivatives of 1,3-diarylpyrazolines for polyamide, quaternary salts of 7-methoxy-2-benzimidazol-2'-ylbenzofuran or of derivatives form the class of the 7-[1',2',5'-triazol-1'-yl]-3-[1'',2'',4''-triazol-1''-y] coumarins for polyacrylonitrile. Example of brighteners suitable for polyester are products of the class of the substituted styryls, ethylenes, thiophenes, naphthalenedicarboxylic acids or derivatives thereof, stilbenes, coumarins and naphthalimides.

It is preferred that laundry compositions herein also contain enzymes to enhance their through-the-wash cleaning performance on a variety of soils and stains. Amylase and protease enzymes suitable for use in detergents are well known in the art and in commercially available liquid and granular detergents. Commercial deterslye enzymes (preferably a mixture of amylase and protease) are typically used at levels of from about 0.001 to about 2 weight percent, and higher, in the present cleaning compositions.

Detergent formulations of this invention may contain minor amounts of other commonly used materials in order to enhance the effectiveness or attractiveness of the product. Exemplary of such materials are soluble sodium carboxymethyl cellulose or other soil redeposition inhibitors; benzotriazole, ethylene thiourea, or other tarnish inhibitors; perfume; fluorescers; dyes or pigments; brightening agents; enzymes; water; alcohols; other builder additives, such as the water soluble salts of ethlendiaminetetraacetic acid, N-(2-hydroxyethyl)-ethylenediaminetriacetic acid; and pH adjusters, such as sodium hydroxide and potassium hydroxide. Other optional ingredients include pH regulants, polyester soil release agents, hydrotropes and gel-control agents, freeze-thaw stabilizers, bactericides, preservatives, suds control agents, fabric softeners especially clays and mixtures of clays with various amines and quaternary ammonium compounds and the like. In the built liquid detergent formulations of this invention, the use of hydrotropic agents may be found efficacious. Suitable hydrotropes include the water-soluble alkali metal salts of toluene sulfonic acid, benzene sulfonic acid, and xylene sulfonic acid. Potassium toluene sulfonate and sodium toluene sulfonate are preferred for this use and will normally be employed in concentrates ranging up to about 10 or 12 percent by weight based on the total composition.

It will be apparent from the foregoing that the compositions of this invention may be formulated according to any of the various commercially desirable forms. For example, the formulations of this invention may be provided in granular form, in liquid form, in tablet form of flakes or powders.

Use of these ingredients is within the skill in the art. Compositions are prepared using techniques within the skill in the art.

The invention is not to be limited to any particular method of mixing the chelant and the other ingredients. The chelant may be e.g. mechanically mixed in the detergent in the form of a solid or slurry, or dissolved in a solution of the other ingredients. In addition, the chelant may be admixed with the other ingredient as manufactured, as well as being added simultaneously or separately to an aqueous solution. In any event, the chelant is intended to be used with the other ingredient at the time of application as a cleansing agent.

The following examples are offered to illustrate but not limit the inventions. Percentages, ratios and parts are by weight unless stated otherwise. Examples of the invention (Ex.) are designated numerically, while comparative samples (C.S.), which are not examples of the invention, are designated alphabetically.

EXAMPLE 1

Synthesis of Iminodiacetic Acid-N-2-Hydroxypropyl Sulfonic Acid (IDA HPS)
(Nitrilo-N,N-Bis(Carboxymethyl) N-2-Hydroxypropyl Sulfonic Acid)

A. Synthesis of 3-chloro-2-hydroxypropylsulfonic acid, sodium salt (CHPS)

Epichlorohydrin (one mole, 93 g) is slowly added to an aqueous solution of one mole sodium bisulfite (104 g in about 120 ml water) while maintaining the temperature at about 80° C. The epichlorohydrin is added dropwise over about three hours, and after addition is complete, the mixture is stirred for an additional hour. After the mixture cools to about 20° C., the solids of 3-chloro-2-hydroxypropylsulfonic acid sodium salt formed from the reaction are filtered and analyzed by Nuclear Magnetic Resonance (NMR). The ISC spectra shows peaks at 69.99 ppm, 56.97 ppm, and 51.18 ppm from TMS (tetramethyl silane) and the proton spectrum shows, three groups of peaks centering at 2.95, 3.58 and 4.17 ppm (from TMS), in a 2:2:1 ratio respectively, consistent with the structure of CHPS.

B. Reaction of CHPS with iminodiacetic acid

A sample of 0,118 mole (15.8 g) iminodiacetic acid (IDA) is dissolved with about 15 ml water and 0.18 mole (14.40 g) 50 weight percent sodium hydroxide. The pH is maintained at about 10 using 50 percent NaOH addition during the addition of CHPS. (The reaction mixture is maintained at about 50° C. throughout.) Then 23.3 g CHPS solids are slowly added to the stirred solution over about an hour. CHPS addition rate is such that temperature does not exceed 55° C. After addition is completed, the temperature is held at 55° C. for about two additional hours. Proton NMR shows peaks at centered at 400 ppm (1 proton), 3.18 ppm (4 protons), 2.80 ppm (2 protons); and a pair of associated multiplets between 2.38 and 2.74 ppm (2 protons) from TMS. A small peak at 3.33 ppm represents a remaining amount of IDA; and carbon NMR shows peaks at 57.83, 61.72, 63.17, and 67.67, with one carbonyl peak at 181.39 ppm from TMS and consistent with the structure of iminodiacetic acid-N-2-hydroxypropylsulfonic acid (IDA HPS) along with traces of the starting materials. (There is a small peak at 52.27 ppm from TMS indicating a remaining trace of IDA.) The material is evaluated without further purification.

A small portion of the reaction mixture from the synthesis of IDA-HPS is saturated with $HC_1$ (hydrochloric acid) to precipitate all NaCl (sodium chloride) and then dried by rotary evaporation. The dried solids are redissolved in deionized water and again taken to dryness. The solids are then dissolved in deionized water at about 60° C., and the pH is adjusted to approximately 10 using 20 percent NaOH. The solution is then evaporated to a syrupy consistency and then slowly added to boiling isopropyl alcohol with vigorous stirring. After cooling, the alcohol layer is decanted, and the aqueous layer is dried in vacuo. The IDA HPS solids isolated contain no traces of starting materials detectable by proton NMR. Performance of the product in peroxide stabilization tests is comparable to the purified product, indicating that the IDA impurity does not interfere with performance.

EXAMPLE 2

Chelation Capacity of Iminodiacetic Acid-N-2-Hydroxypropyl Sulfonic Acid

Chelation of copper is used to show that the compound is capable of chelating metals. Titration is performed using ammonium purpurate indicator for complexometric titration commercially available from Aldrich Chemical Co., Inc. under the trade designation Murexide as the indicator at approximately pH 8, and using sodium acetate as buffer. Titration of 3.3 mg IDA-HPS (0.012 mMoles) in 100 ml water with 0.01 molar copper chloride gives an endpoint of 1.19–1.21 ml (0.012 mMoles), representing a 1:1 chelation of copper.

EXAMPLE 3 AND COMPARATIVE SAMPLES A–D

Peroxide Stabilization Screening Test

To evaluate the performance of various chelating agents in stabilizing peroxide in simulated wash conditions, the following procedure is followed for each comparative sample and example:

1. Solutions are prepared by
   A. Mixing a synthetic detergent water to contain the following components:
      1) 750 ppm dodecyl benzene sulfonate
      2) 500 ppm linear alkyl polyglycol ether
      3) 500 ppm sodium carbonate
      4) 2000 ppm sodium sulfate
      5) 150 ppm sodium metasilicate
      6) 10 ppm silicon based antifoaming agent commercially available from Union Carbide Corp. under the trade designation SAG Mark X.
   B. Preparing a solution of metals (mixed metals solution) that when added to the detergent water in the test vessels will provide a concentration of 1 ppm each Cu(II), Fe(III), and Mn(II), 200 ppm calcium hardness (expressed as $CaCO_3$) and 50 ppm magnesium hardness (expressed as $CaCO_3$). The solutions are sufficiently concentrated to avoid any significant dilution of the detergent water when the solutions are mixed.
   C. Preparing 1 weight percent active (as the acid form) of each of the candidate chelants to be screened in Example 3 and Comparative Samples A–D. When solution pH is less than about 2 or above about 12, the pH of the solution is adjusted to about 8–10 during preparation using NaOH and/or $HC_1$ solutions.
2. Preparing a temperature regulated water bath and a means of stirring test vessels while immersed in the water bath. Preheat the bath at 60° C.
3. To each test vessel (125 erlenmeyer flasks), rapidly adding in the following order: 1) 1 ml of the 1 percent test chelant solution to provide a chelant level of 100 ppm test concentration, 2) 100 ml detergent water described in 1A, 3) mixed metal salts solution as described in 1B, 4) 1 ml standardized 3 percent hydrogen peroxide solution to provide the equivalent of approximately 1200 ppm sodium perborate tetrahydrate in the final test solution.
4. Immediately placing the solution on the water bath/stirrer, beginning timing from the moment of peroxide addition.
5. Removing samples for analysis at 1, 6, 12, 18 and 24 minutes after peroxide addition to follow the degradation of the peroxide.
   a. The samples removed for analysis are immediately acidified using sulfuric acid to halt any further decomposition of peroxide and stops $H_2O_2$ (peroxide) degradation in data analysis.
   b. Peroxide is analyzed via iodometric titration. (KI (potassium iodide) is added; titration uses standardized sodium thiosulfate with an endpoint indicated by platinum electrode potential break point) and expressed as percent of the original peroxide remaining.

Each analysis is performed in duplicate.

The following samples are evaluated using the outlined procedure:
Ethylenediaminetetraacetic acid (EDTA)
Nitrilotriacetic acid (NTA)
Iminodiacetic acid-N-2-hydroxypropylsulfonic acid (IDAHPS)
Isoserinediacetic acid (ISDA)
Control (no added chelant)
Results are shown in Table 1.

TABLE 1

| | Results at: | 6 min. | 12 min. | 18 min. | 24 min. |
|---|---|---|---|---|---|
| C.S. A | EDTA | 81% | 66% | 58% | 55% |
| C.S. B | NTA | 63% | 35% | 21% | 15% |
| EX. 3 | IDAHPS | 77% | 58% | 44% | 39% |
| C.S. C | ISDA | 65% | 31% | 16% | 8% |
| C.S. D | CONTROL* | 53% | 21% | 12% | 7% |

*The control (C.S. D) has the same ingredients including peroxide as in CS. A–C and Ex. 3 but no added chelant.
% means percent of original concentration remaining after the stated time.

The results from the peroxide stability test show that IDAHPS (a chelate of the invention) stabilizes peroxide better than NTA and ISDA and approaches the performance of EDTA which is widely used for this purpose.

EXAMPLE 4

Biodegradability Screening Via ASTM D2667 Semi-Continuous Activated Sludge Test

The procedure of ASTM D-2665-82 is used to determine the inherent biodegradablity of the compounds tested in Example 3 and Comparative Samples A–D. Copper titration value (as described in Example 2) is used to measure the extent of biodegradation of the chelating agents during the procedure. The analyses are performed daily for a period of 28 days.

Results of the biodegradation screening:

IDAHPS showed 80 percent loss of chelation capacity (indicating degradation) within 25 days while NTA showed greater than 80 percent degradation within 8 days, and ISDA showed greater than 80 percent degradation within 18 days.

No measurable loss of EDTA is noted within the 28 day test period.

A control is used to verify the abscence of interfering chelating substances in the test.

These results of the biodegradability test show that the IDAHPS material is inherently biodegradable and could be expected to be utilized by organisms in a municipal treatment facility after an acceptable acclimation period. (Detergent manufacturers have expressed a desire for products that will be at least 80 percent biodegraded within 28 days.)

What is claimed is:

1. A method of cleaning a hard surface comprising contacting the surface with a composition comprising an organic solvent and a compound of the formula

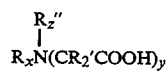

wherein R is an alkyl having at least one —$SO_3H$ group and at least one —OH group;
each R' is independently selected from hydrogen, an unsubstituted or inertly substituted alkyl group; an alkyl group substituted with a carbonyl group, with a carboxylic acid, salt or complexed carboxyl group, a hydroxyalkyl group or an alkoxy groups;
R" is a hydroxyalky group;
x is an integer of 1 or 2;
y is an integer of 1 or 2;
z is an integer of 0 or 1 such that the sum of x, y, and z is 3;
and then removing a portion of the composition from the hard surface.

2. The method of claim 1 wherein the solvent has a boiling point of at least about 90° C.

3. The method of claim 2 wherein the solvent is a alkyl aromatic solvent wherein the alkyl group has about 6 to about 9 carbon atoms.

4. The method of claim 2 wherein the solvent comprises alkyl benzene wherein the alkyl group has about 6 to about 9 carbon atoms, a $C_{10}$–$C_{12}$ alpha olefin, benzyl alcohol, n-hexanol, phthalic acid ester or combination thereof.

5. The method of claim 2 wherein the solvent comprises a diol having from about 6 to about 16 carbon atoms.

6. The method of claim 2 wherein the solvent comprises a glycol ether.

7. The method of claim 2 wherein the solvent is present in a solvent to chelant ratio by weight of from about 2/3 to 2/1.

8. The method of claim 1 wherein the chelant is present in an amount of from about 0.1 to about 5 weight percent.

* * * * *